United States Patent [19]

Fujii et al.

[11] Patent Number: 4,746,737
[45] Date of Patent: May 24, 1988

[54] PHENYL GUANIDINOBENZOATE DERIVATIVES WHICH HAVE PROTEASE INHIBITORY ACTIVITY

[75] Inventors: Setsuro Fujii, Kyoto; Eizou Hattori, Sakado; Mitsuteru Hirata, Saitama; Koichiro Watanabe, Niiza; Tomio Ohta, Sayama; Nobuo Yokoo, Sayama; Masahiko Nagakura, Sayama, all of Japan

[73] Assignee: Kowa Co., Ltd., Nagoya, Japan

[21] Appl. No.: 886,046

[22] Filed: Jul. 16, 1986

[30] Foreign Application Priority Data

Jul. 26, 1985 [JP] Japan .................. 60-165236

[51] Int. Cl.$^4$ .................. C07D 243/08; C07D 265/30
[52] U.S. Cl. .................. 540/575; 540/460; 544/121; 544/169; 544/357; 544/360; 544/372; 544/386; 544/387; 544/388; 548/337; 548/341; 564/155; 564/164
[58] Field of Search .............. 544/386, 387, 388, 121, 544/169, 357, 360, 372; 540/575, 460; 548/337, 341; 564/155, 164

[56] References Cited

FOREIGN PATENT DOCUMENTS 67561 12/1982 European Pat. Off. ............ 544/386

Primary Examiner—Donald G. Daus
Assistant Examiner—Cecilia Shen
Attorney, Agent, or Firm—Oblon, Fisher, Spivak, McClelland & Maier

[57] ABSTRACT

Novel benzoyl esters of the following formula (I), and acid addition salts thereof,

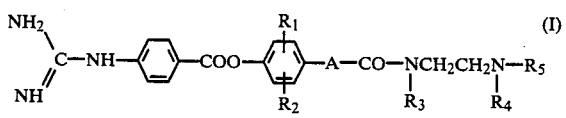

in which $R_1$ and $R_2$ are the same or different and represent a hydrogen atom or a lower alkoxy group, A represents a single bond, a linear or branched lower alkylene group, a lower alkenylene group, $R_3$ and $R_4$ are the same or different and represent a hydrogen atom or a lower alkyl group, or $R_3$ and $R_4$ join together to form a lower alkylene group, $R_5$ represents a group of the formula, $-X-(CO)_n-Y$ in which X represents a single bond, a linear or branched lower alkylene group or an alkenylene group, n is 0 or 1, Y represents a hydrogen atom, a cycloalkyl group, an aryl group, a hydroxyl group, a lower alkoxy group and the like are prepared by reacting para-nitrobenzoic acid or its derivative with a compound of the general formula (III) or its derivative

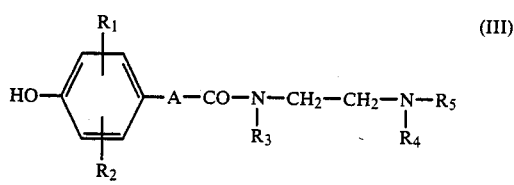

to obtain a compound of the general formula (IV)

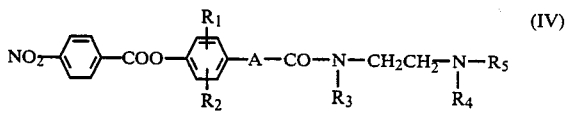

followed by reducing the compound of the formula (IX)

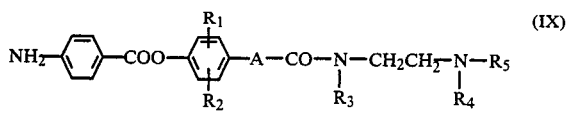

and subjecting the compound (IX) to guanidylation reaction, or by reaction para-guanidinobenzoic derivative with compound (III) or its derivative.

The benzoyl esters have strong anti-trypsin activity, anti-thrombin activity and anticoagulant activity with low toxicity and are useful as a medicine for treatment of pancreatitis and disseminated intravascular coagulation (DIC).

29 Claims, No Drawings

PHENYL GUANIDINOBENZOATE DERIVATIVES WHICH HAVE PROTEASE INHIBITORY ACTIVITY

BACKGROUND OF THE INVENTION

1. Field of the Invention

This invention relates to novel benzoyl esters and acid addition salts thereof which have the inhibitory activities against proteases and are thus useful as a medicine.

2. Description of the Prior Art

It is known that various guanidinobenzoic acid derivatives have the action of inhibiting proteases including thrombin and plasmin and serve as an anticoagulant.

However, the efficacy of the known guanidinobenzoic acid derivatives is not necessarily satisfactory and, therefore, there is a demand of novel compounds having a better efficacy.

SUMMARY OF THE INVENTION

Under these circumstances in the art, the present inventors made intensive studies and, as a result, found that novel benzoyl esters of the following general formula (I) had excellent medical efficacies

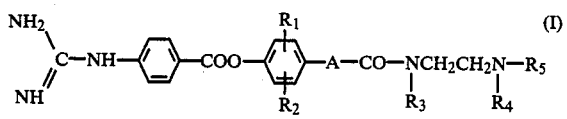

in which $R_1$ and $R_2$ are the same or different and represent a hydrogen atom or a lower alkoxy group, A represents a single bond or a linear or branched lower alkylene or alkenylene group, $R_3$ and $R_4$ are the same or different and represent a hydrogen atom or a lower alkyl group, or $R_3$ and $R_4$ join together to form a lower alkylene group, $R_5$ represents a group of the formula, $-X-(CO)_n-Y$ in which X represents a single bond, a linear or branched lower alkylene group or an alkenylene group, n is 0 or 1, Y represents a hydrogen atom, a cycloalkyl group, an aryl group, a hydroxyl group, a lower alkoxy group, an aralkoxy group, a group of the formula,

in which $R_6$ and $R_7$ are the same or different and represent a hydrogen atom, a linear or branched lower alkyl group, an aryl group, a lower acyl group, an alkoxycarbonyl group, an aralkylcarbonyl group, an alkoxycarbonylalkyl group, an aminoalkyl group, a monoalkylaminoalkyl group, a dialkylaminoalkyl group, or join together to form a heterocyclic ring along with the adjacent nitrogen atom, or forms a ring containing a hetero-atom in combination with $R_4$.

Thus, the present invention provides benzoyl esters of the formula (I) and acid addition salts thereof, which are useful as medicines.

DETAILED DESCRIPTION OF THE INVENTION AND PREFERRED EMBODIMENTS

In the compound (I) of the invention, the lower alkoxy group represented by $R_1$ and $R_2$ should preferably have from 1 to 6 carbon atoms and include, for example, methoxy group, ethoxy group, n-propoxy group, isopropoxy group and the like. These groups should preferably be substituted at the 3 position or the 3 and 5 positions of the phenyl group. The lower alkylene or alkenylene group represented by A should preferably be linear or branched groups having from 1 to 6 carbon atoms, of which methylene group, ethylene group, methylmethylene group, trimethylene group, propylene group, vinylene group and propenylene group are most preferable.

The lower alkyl group in $R_3$ and $R_4$ should preferably have from 1 to 6 carbon atoms. The lower alkylene group represented by $R_3$ and $R_4$ in combination has from 1 to 6 carbon atoms. Examples of a ring formed by the lower alkylene group along with two adjacent nitrogen atoms include imidazolidine, piperazine, homopiperazine and the like.

In the compound (I) of the invention, when $R_5$ represents a group of the formula, $-X-(CO)_n-Y$, X represents the same alkylene group, alkenylene group as A described above or single bond. The cycloalkyl group represented by Y should preferably have from 3 to 8 carbon atoms, of which a cyclohexyl group is most preferred. The aryl group may be a phenyl group or a naphthyl group which may have a substituent. The lower alkoxy group may be those represented by $R_1$ and $R_2$. The aralkoxy group is most preferably a benzyloxy group. When Y represents

$R_6$ and $R_7$ indepedently represent a lower alkyl group, an acyl group, an alkoxycarbonyl group, an aralkoxycarbonyl group, an alkoxycarbonylalkyl group, an aminoalkyl group, a monoalkylaminoalkyl group, a dialkylaminoalkyl group, in which the alkyl group or moiety should preferably have from 1 to 6 carbon atoms. The aryl group should preferably be those indicated before. The heterocyclic ring formed by bonding of $R_6$ and $R_7$ along with adjacent nitrogen atoms includes, for example, pyrrolidine, piperidine, morpholine, piperazine, homopiperazine and the like. These heterocyclic rings may have substituents. Examples of the substituents include a lower alkyl group, a hydroxyl group, a lower alkoxy group, a lower alkoxycarbonyl group, an oxo group and the like.

Examples of the ring formed by $R_4$ and $R_5$ along with the adjacent nitrogen atom and containing a heteroatom include piperidine, morpholine and the like.

The compound (I) of the invention is prepared, for example, according to any of the following processes.

(1) A process in which para-nitrobenzoic acid of the following formula (II) or its reactive derivative

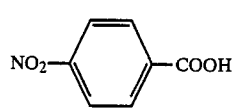

is reacted with a compound of the general formula (III) or its reactive derivative

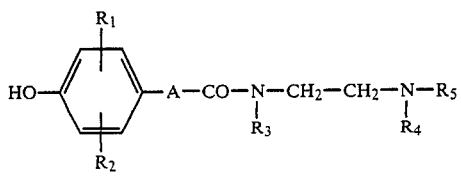

in which R₁, R₂, R₃, R₄, R₅ and A have, respectively, the same meanings as defined before, thereby obtaining a compound of the general formula (IV)

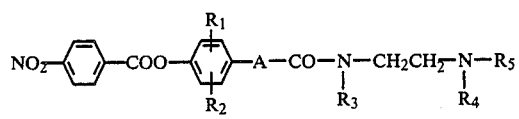

in which R₁, R₂, R₃, R₄, R₅ and A have, respectively, the same meanings as defined before. Subsequently, the compound (IV) is reduced for conversion of the nitro group into an amino group, followed by guanidylation to obtain compound (I).

(2) A process of reacting paraguanidinobenzoic acid of the following formula (V) or its reactive derivative

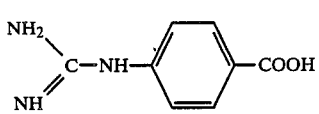

with compound (III) or its reactive derivative.

The starting compound (III) in the above processes can be prepared, for example, by a procedure which comprises reacting a compound of the formula (VII)

$$Z-R_5 \qquad (VII)$$

in which Z represents a halogen atom or a sulfonic group and R₅ has the same meaning as defined before, with a compound of the formula (VI)

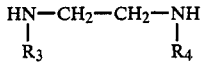

in which R₃ and R₄ have, respectively, the same meanings as defined before, followed by further reaction with a carboxylic acid of the following general formula (VIII) or its reactive derivative

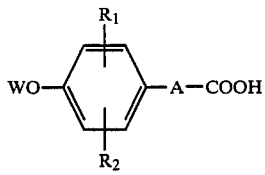

in which W represents a hydrogen atom or a protective group for the hydroxyl group, and R₁, R₂ and A have, respectively, the same meanings as defined before, and elimination of the protective group, if necessary.

The compound of the formula (V) is prepared, for example, by reacting a cyanamide with p-aminobenzoic acid or a compound obtained by protecting the carboxyl group of p-aminobenzoic acid, and eliminating the protecting group, if necessary.

The reaction between the carboxylic acid (II) or (V) and the phenol (III) is effected according to ordinary dehydration condensation reactions. More particularly, several processes are known including (a) a process in which free carboxylic acids or acid addition salts thereof and the phenols or acid addition salts thereof are reacted in the presence of a catalyst or a condensing agent, (b) a process in which reactive derivatives of carboxylic acids are reacted with the phenols, and (c) a process of reacting free carboxylic acids with reactive derivatives of the phenols.

The catalysts used in the process (a) include, for example, acid catalysts such as sulfuric acid, hydrochloric acid, p-toluenesulfonic acid, phosphorus oxychloride, polyphosphoric acid, boron trifluoride and the like. The condensing agents include, for example, diphenylphosphorylazide, dicyclohexylcarbodiimide, N,N'-disuccinimidylcarbamate, N,N'-carbonyldiimidazole, 1-(3-dimethylaminopropyl)-3-ethylcarbodiimide, dimethylformamide dineopentylacetal, dimethylformamide diethylacetal, N,N-dimethylphosphoramidic chloride, phenyl dichlorophosphate and the like. Basic catalysts such as dimethylaminopyridine, pyrrolidone, pyridine and the like may be used together with the condensing agents described above.

The reaction conditions vary depending on the type of catalyst or condensing agent. For instance, where dicyclohexylcarbodiimide serving as a condensing agent is used, carboxylic acid (II) or (V) and dicyclohexylcarbodiimide are reacted in a solvent, which is then added to a solution of phenol (III), followed by agitation in the presence or absence of a base at a temperature of −30° to 100° C. for several hours to several days to complete the reaction.

The solvents used for this purpose may be ordinary organic solvents including, for example, pyridine, dimethylformamide, chloroform, dichloromethane, carbon tetrachloride, benzene, diethyl ether, dioxane, tetrahydrofuran, ethyl acetate, acetonitrile, dimethylsulfoxide, and water. Examples of the bases include triethylamine, diisopropylethylamine, di-t-butylamine, dimethylaminopyridine, pyrrolidinopyridine, N-methylmorpholine, 1,8-diazabicyclo[5.4.0]-7-undecene, and the like.

The reactive derivatives of carboxylic acids (II) or (V) in the process (b) include, for example, acid halides such as acid chlorides, acid bromides and the like; acid anhydrides; mixed acid anhydrides with trifluoroacetic acid, methanesulfonic acid, benzenesulfonic acid, isobutoxyformic acid and the like; and onium salts such as 2-bromo-1-pyridinium iodide, 2-chloro-3,5-dinitropyridine, 2-chloro-1-methylpyridinium iodide and the like; and active esters such as p-nitrophenyl ester, N-O-succinimide esters and the like.

The reaction conditions vary depending on the type of reactive derivative. With acid chlorides, for example, the reaction between an acid chloride and a phenol (III) completes by agitating in a solvent in the presence or absence of a base at 0° to 100° C. for several hours to several days.

The solvents used for the reaction include, for example, chloroform, dichloromethane, carbon tetrachloride, benzene, ethyl acetate, tetrahydrofuran, dioxane, pyridine, acetonitrile, dimethylformamide, dimethylsulfoxide, and the like. Examples of the base include triethylamine, diisopropylethylamine, di-t-butylamine, pyridine, dimethylaminopyridine, pyrrolidinopyridine, N-methylmorpholine, 1,8-diazabicyclo[5.4.0]-7-undecene and the like.

The reactive derivatives of the phenol (III) in the process (c) may be trifluoroacetic esters of the phenol or compounds of the formula

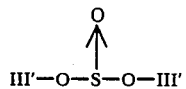

in which each III' represents a hydroxyl residue of the compounds of the formula (III).

The method of reducing the nitro group of the compound (IV) into an amino group in the process (1) may be a catalytic reduction method, a method of reduction with a metal such as iron or zinc in an acidic solution, a reduction method using a metal hydride such as lithium aluminium hydride or sodium boron hydride, and a method using a reducing agent such as hydrosulfite, ferrous sulfate and aqueous ammonia, zinc and water, zinc and sodium hydroxide, aqueous ammonia and hydrogen sulfide, or the like. Of these, a catalytic reduction method is most preferable.

The catalysts used for the catalytic reduction include, for example, platinum, Raney nickel, platinum-carbon, palladium-carbon, rhodium-alumina, platinum sulfide-carbon, and the like.

The reaction proceeds in a solvent in the presence of a catalyst at normal temperatures under normal pressures by passage of a hydrogen gas for several minutes to severl tens hours. The reaction may be accelerated by increasing the temperature and pressure. The hydrogen source may be, aside from hydrogen gas, formic acid, ammonium formate and the like. The solvents may be, for example, acetic acid, methanol, ethanol, dioxane, dimethylformamide, water, and the like.

The guanidylation of the resultant amino compound is effected by subjecting the compound to reaction with cyanamide or 3,5-dimethyl-1-guanylpyrazol. With cyanamide, cyanamide is reacted with the amino compound in an acidic condition of hydrochloric acid at 0° to 100° C. for 1 to 30 hours. Examples of the solvent include water, tetrahydrofuran, dioxane, acetonitrile, dimethylsulfoxide, dimethylformamide and the like.

The thus obtained compound (I) of the invention may be converted, if necessary, into acid addition salts by a usual manner. Examples of the acid include inorganic acids such as sulfuric acid, hydrochloric acid, nitric acid, phosphoric acid, hydrobromic acid an the like; and organic acids such as acetic acid, lactic acid, succinic acid, tartaric acid, malic acid, citric acid, methanesulfonic acid, benzenesulfonic acid, toluenesulfonic acid and the like.

Typical compounds (I) of the invention were tested with respect to the enzyme inhibitory activities, anticoagulant activity and toxicity with the following results.

(1) Trypsin inhibitory activity

To 0.1 ml of a dimethylsulfoxide solution of a compound to be tested were added 0.3 ml of a 0.1M trishydrochloric acid buffer solution (pH 8.0) containing 10 mM of calcium chloride and 0.1 ml of a solution of 50 ng/ml of trypsin dissolved in the buffer solution, followed by incubation at 37° C. and 10 minutes. Thereafter, 5 microliters of a dimethylformamide solution of 10 mM Boc-Phe-Ser-Arg-MCA, followed by reaction at 37° C. for 30 minutes and addition of 0.5 ml of a 10% acetic acid solution to stop the reaction. The fluorescence of produced 7-amino-4-methylcumarin was measured by the use of a fluorometer (Fluorometer 650-40, by Hitachi Ltd.) under conditions of an excitation wavelength of 380 nm, a wavelength of the fluorescence of 460 nm and a slit width of 2 mm.

The inhibition rate of the respective compounds to be tested was calculated according to the following equation.

$$\text{Inhibition rate (\%)} = \frac{(E - S) - (T - S)}{E - S} \times 100$$

in which T represents a measured value of "test specimen+enzyme+substrate", E represents a measured value of "enzyme+substrate", and S represents a measured value of "substrate".

From the equation, a concentration of the test compound for 50% inhibition was determined with the results shown in Table 1.

(2) Thrombin inhibitory activity

To 0.1 ml of a dimethylsulfoxide solution of each of compounds to be tested were added 0.3 ml of a 0.1M phosphate buffer solution (pH 7.4) and 0.1 ml of a thrombin solution containing 100 mu/ml of thrombin in the buffer solution, followed by incubation at 37° C. for 10 minutes. To the solution was added 5 ml of dimethylformamide solution of 10 mM Boc-Val-Pro-Arg-MCA for reaction at 37° C. for 30 minutes. Thereafter, the inhibition rate was calculated similar to the case of trypsin. The 50% inhibition rates of the respective compounds tested are shown in Table 1.

(3) Anticoagulant activity

A compound to be tested was dissolved into a physiological saline solution so as to have the final concentration of $1 \times 10^{-4}$M and then cooled down by ice. A 0.05 ml of the thus prepared solution was added with 0.5 ml of rat's blood, followed by subjecting the obtained solution to a thrombelastograph (manufactured by Hellige Company). The blood coagulation time (r+k value) was determined by the obtained thrombelastogram. The results are shown in Table 1.

(4) Acute toxicity

The acute toxicity ($LD_{50}$) was determined by intravenous administration to mice with the results shown in Table 2.

TABLE 1

| Compounds to be tested (Example No.) | Concentration for 50% inhibition (M) | | Blood coagulation time (min.) |
|---|---|---|---|
| | trypsin | thrombin | |
| 2 | $2 \times 10^{-8}$ | $2 \times 10^{-7}$ | $26.7 \pm 3.3$ |
| 6 | $6 \times 10^{-9}$ | $4 \times 10^{-7}$ | $15.3 \pm 3.1$ |
| 7 | $7 \times 10^{-9}$ | $4 \times 10^{-7}$ | $9.7 \pm 0.3$ |
| 8 | $7 \times 10^{-8}$ | $4 \times 10^{-6}$ | — |
| 9 | $1 \times 10^{-8}$ | $4 \times 10^{-7}$ | 18.5 |
| 10 | $2 \times 10^{-8}$ | $4 \times 10^{-7}$ | 10 |
| 11 | $4 \times 10^{-7}$ | $9 \times 10^{-6}$ | — |
| 12 | $1 \times 10^{-8}$ | $4 \times 10^{-7}$ | 14.5 |
| 13 | $2 \times 10^{-8}$ | $2 \times 10^{-7}$ | $21 \pm 3.9$ |
| 14 | $1 \times 10^{-7}$ | $3 \times 10^{-6}$ | 9.8 |
| 22 | $4 \times 10^{-8}$ | $3 \times 10^{-7}$ | $20.5 \pm 0.8$ |
| 25 | $2 \times 10^{-8}$ | $1 \times 10^{-7}$ | $18.8 \pm 1.2$ |
| 27 | $4 \times 10^{-8}$ | $5 \times 10^{-7}$ | $19.2 \pm 2.3$ |
| 29 | $3 \times 10^{-8}$ | $2 \times 10^{-7}$ | $34.8 \pm 5.5$ |
| 30 | $3 \times 10^{-8}$ | $2 \times 10^{-7}$ | $16.5 \pm 1.6$ |
| 33 | $2 \times 10^{-8}$ | $1 \times 10^{-7}$ | $32 \pm 2.5$ |
| 34 | $1 \times 10^{-8}$ | $3 \times 10^{-7}$ | $41.3 \pm 3.9$ |
| 37 | $4 \times 10^{-8}$ | $8 \times 10^{-8}$ | $46.5 \pm 4.5$ |
| 38 | $3 \times 10^{-8}$ | $1 \times 10^{-7}$ | $34.2 \pm 1.6$ |
| Reference compound A* | $5 \times 10^{-8}$ | $3 \times 10^{-6}$ | $9.8 \pm 0.6$ |

TABLE 1-continued

| Compounds to be tested (Example No.) | Concentration for 50% inhibition (M) | | Blood coagulation time (min.) |
|---|---|---|---|
| | trypsin | thrombin | |
| Reference compound B** | $4 \times 10^{-7}$ | $3 \times 10^{-6}$ | $9.8 \pm 1.6$ |

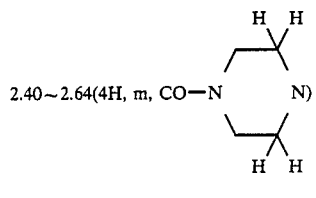

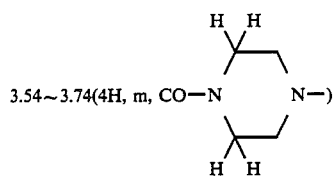

TABLE 2

| Compounds to be tested (Example No.) | $LD_{50}$ (mg/kg) |
|---|---|
| 2 | 150–200 |
| 6 | 150–200 |
| 7 | 100–150 |
| 8 | 25–50 |
| 9 | 150–200 |
| 10 | 150–200 |
| 11 | 50–100 |
| 12 | 100–150 |
| 13 | 50–100 |
| 14 | 50–100 |
| Reference compound A | 280 |
| Reference compound B | 313 |

As will be apparent from the above results, the compounds (I) of the present invention have strong antitrypsin activity, anti-thrombin activity and anticoagulant activity with low toxicity and are thus useful as a medicine for treatment of pancreatitis and disseminated intravascular coagulation (DIC).

When the compounds (I) of the invention are used as the medicine, they can be prepared, along with suitable excipients, carriers, diluents and the like, into tablets, capsules, granules, powder and injections and can be orally or parenterally dosed.

The present invention is more particularly described by way of examples.

EXAMPLE 1

Preparation of 4-[4-(carbamoylmethyl)piperazinocarbonylmethyl]phenyl 4-guanidinobenzoate.dihydrochloride (a) 386 mg of 1-carbamoylmethyl-4-(4-hydroxyphenyl)acetylpiperazine and 0.24 ml of triethylamine were suspended in 5 ml of chloroform, to which 310 mg of 4-nitrobenzoyl chloride, followed by stirring overnight at room temperature.

The reaction solution was concentrated under reduced pressure, to which water was added and the resultant crystals were collected by filtration, followed by washing with water and ether and drying. The resultant product was recrystallized from chloroform-methanol-ether to obtain 540 mg (yield 91.9%) of 4-[4-(carbamoylmethyl)piperazinocarbonylmethyl]phenyl 4-nitrobenzoate in the form of light yellow crystals having a melting point of 192° to 196° C.

IR (KBr): $cm^{-1}$ 1730, 1679, 1641, 1515, 1275.

$^1$H-NMR (DMSO-d6): δ

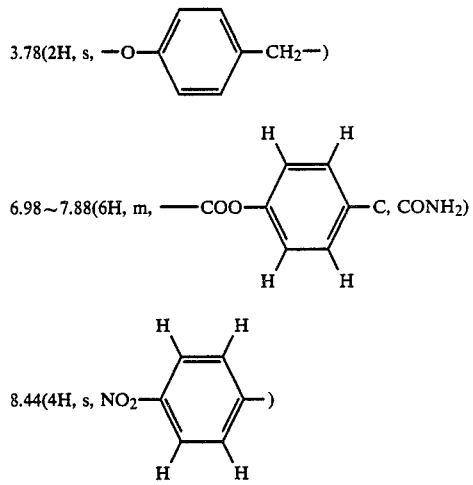

(b) 520 mg of the nitro compound obtained in (a) was dissolved in 5 ml of acetic acid, to which 100 mg of 10% palladium-carbon was added, followed by catalytic reduction at room temperature for 1.5 hours.

After completion of the reaction, the catalyst was removed by filtration and concentrated under reduced pressure, to which ether was added to collect the resultant crystals to obtain, as colorless crystals having a melting point of 235° to 237° C., 410 mg (yield 84.8%) of 4-[4-(carbamoylmethyl)piperazinocarbonylmethyl]phenyl 4-aminobenzoate.

IR (KBr): $cm^{-1}$ 3320, 1708, 1687, 1646, 1628, 1595, 1278, 1194, 1161.

$^1$H-NMR (DMSO-d6): δ

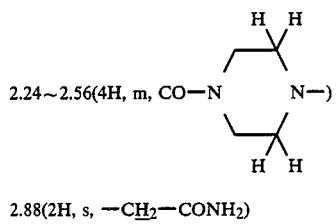

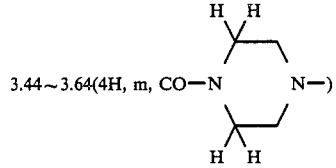

-continued 3.75(2H, s, 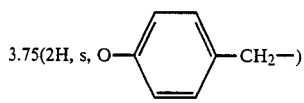O—⌬—CH₂—)

6.16(2H, br.s, NH₂—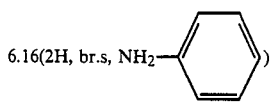)

6.68(2H, d, N—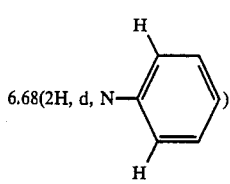)

7.10~7.42(6H, m, —COO—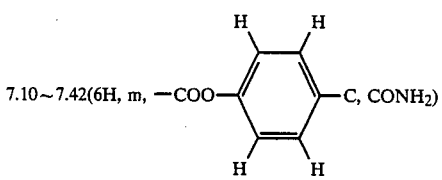—C, CONH₂)

7.85(2H, d, N—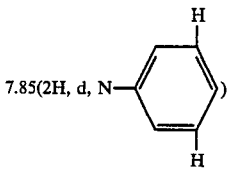)

(c) 396 mg of the amino compound obtained in (b) was dissolved in 1.5 ml of 2N hydrochloric acid, to which 420 mg of cyanamide was added and stirred at 50° C. for 5 hours.

The reaction solution was concentrated under reduced pressure to which acetone was added, followed by collecting an oily substance. This substance was subjected to a column of Sephadex LH-20 and eluted with methanol. Fractions containing the intended product were collected and concentrated under reduced pressure, to which acetonitrile was added. The resulting crystals were collected by filtration. The crystals were recrystallized from methanol-acetonitrile to obtain 199 mg (yield 38.9%) of the intended dihydrochloride in the form of colorless crystals having a melting point of 218° to 220° C. (decomposed).

IR (KBr): cm⁻¹ 3354, 1713, 1673, 1641, 1593, 1568, 1264, 1137.

¹H-NMR (DMSO-d6): δ

3.12~3.62(10H, m, N—CH₂×5)

3.86(2H, s, 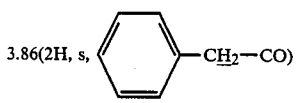—CH₂—CO)

7.20~7.60(6H, m, N—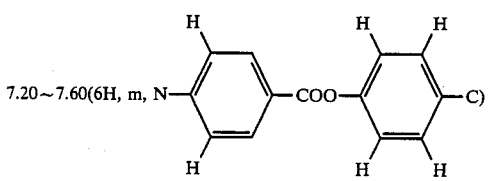—COO—⌬—C)

-continued 7.75(1H, br.s, —CONH)

8.05(4H, br.s, 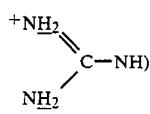)

8.14~8.32(3H, m, —CONH, N—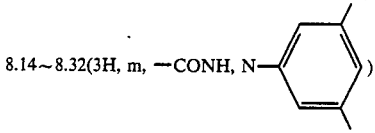)

10.88(1H, s, 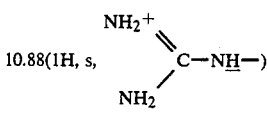)

EXAMPLE 2

Preparation of 4-[4-(carbamoylmethyl)piperazinocarbonyl]phenyl 4-guanidinobenzoate.dihydrochloride 7.54 g of 4-guanidinobenzoic acid dihydrochloride and 7.23 g of dicyclohexylcarbodiimide were added to 100 ml of pyridine, followed by stirring under ice-cooling conditions for 1.5 hours (reaction solution A).

10.5 g of 1-carbamoylmethyl-4-(4-hydroxybenzoyl)-piperazine hydrochloride and 0.43 g of 4-dimethylaminopyridine were dissolved in 210 ml of water, to which the reaction solution A was dropped under ice-cooling conditions while stirring. After completion of the dropping, the reaction solution was stirred under ice-cooling conditions for 1 hour, followed by further stirring at room temperature overnight. A fresh reaction solution A was dropped into the resultant reaction solution under ice-cooling conditions and stirred overnight.

Insoluble matters were removed from the reaction solution by filtration and the filtrate was concentrated under reduced pressure, to which 125 ml of water was added and insoluble matters were filtered off. Thereafter, 8.8 g of sodium hydrogencarbonate and then 350 ml of an aqueous saturated sodium hydrogencarbonate solution were added to the resultant filtrate, followed by allowing to stand for 1 hour. The resultant crystals were collected by filtration and washed with an aqueous saturated sodium hydrogencarbonate solution, a saturated saline solution, water, acetone, and ether in this order, thereby obtaining 13.99 g (yield 82.1%) of an intended carbonate.

The carbonate was suspended in 100 ml of methanol, to which 9.7 ml of 6N-HCl/dioxane and then 70 ml of dioxane were added. The resultant crystals were collected by filtration, washed with acetone and ether, and recrystallized from methanol, thereby obtaining 10.58 g of the intended dihydrochloride having a melting point of 185° to 189° C.

Solubility: over 10% (pH 3.57)

IR (KBr): cm⁻¹ 3300, 1726, 1669, 1602, 1570, 1264, 1206.

¹H-NMR (DMSO-d6): δ

3.28–3.52(8H, br., 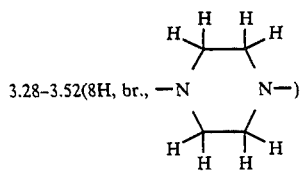)

3.95(2H, br., >N—CH₂CO)

7.37~7.61(6H, m, N— 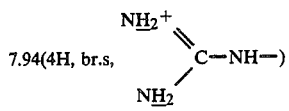 )

7.73(1H, br.s, CONH)

7.94(4H, br.s, 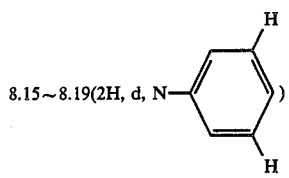)

8.12(1H, br.s, CONH)

8.15~8.19(2H, d, N— 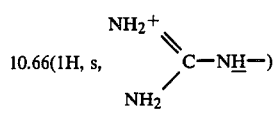 )

10.66(1H, s, 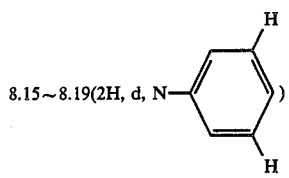)

Elementary Analysis:

| Calculated for | C | H | N |
|---|---|---|---|
| C₂₁H₂₄N₆O₄·2HCl (%): | 50.71 | 5.26 | 16.89 |
| Found (%): | 50.46 | 5.34 | 16.65 |

EXAMPLES 3–38

According to the general procedure of Examples 1 or 2, the following compounds were prepared.

EXAMPLE 3

4-[2-(4-Carbamoylmethylpiperazinocarbonyl)ethenyl]-phenyl 4-guanidinobenzoate.dihydrochloride Melting Point: 225°–227° C. (decomposed).

IR (KBr): cm⁻¹ 3348, 1717, 1683, 1645, 1598, 1569, 1271, 1204.

¹H-NMR (DMSO-d6): δ

3.14~3.74(10H, br.N—CH₂×5)

7.37~7.77(7H, m, N— 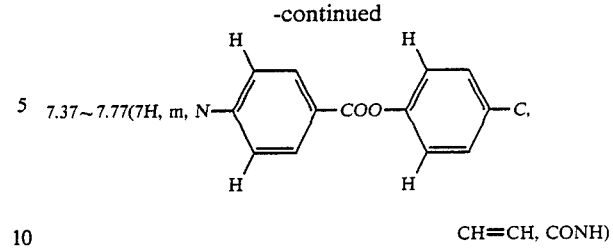 CH=CH, CONH)

7.84~8.34(9H, m, N— 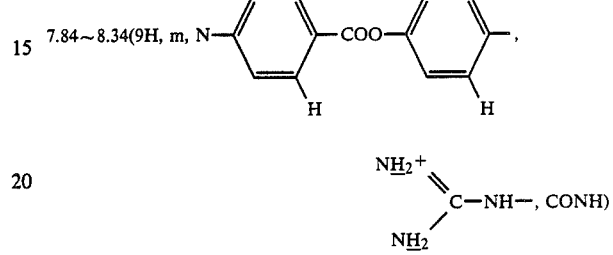, CONH)

10.92(1H, s, 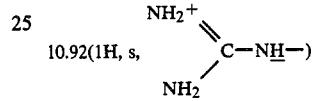)

EXAMPLE 4

4-[4-(Dimethylcarbamoylmethyl)-piperazinocarbonyl]-phenyl 4-guanidinobenzoate.-dihydrochloride White powder IR (KBr): cm⁻¹ 3349, 1729, 1630, 1621, 1565, 1260, 1200.

¹H-NMR (DMSO-d6): δ

2.55(6H, d, CH₃δ)

3.20~4.06(10H, br.N—CH₂×5)

7.40~7.70(6H, m, N— 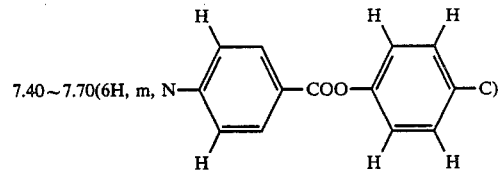)

8.05(4H, br.s, 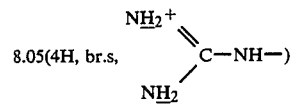)

8.23(2H, d, N— 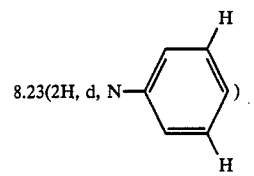)

10.89(1H, s, 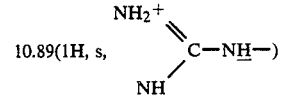)

EXAMPLE 5

4-[2-[4-Carbamoylmethylpiperazinocarbonyl)ethyl]-phenyl 4-guanidinobenzoate.dihydrochloride White powder
IR (KBr): cm$^{-1}$ 3348, 1723, 1673, 1624, 1600, 1567, 1271, 1196.
$^1$H-NMR (DMSO-d6): δ

2.90~3.65(14H,m,N—CH$_2$×5,CH$_2$—CH$_2$)

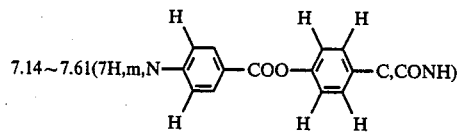

7.14~7.61(7H,m,N—COO—C,CONH)

7.76(1H,br.s,CONH)

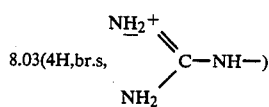

8.03(4H,br.s, C—NH—)

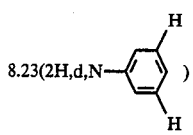

8.23(2H,d,N— )

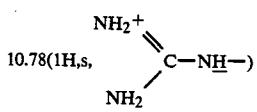

10.78(1H,s, C—NH—)

EXAMPLE 6

4-[4-(Morpholynocarbonylmethyl)piperazinocarbonyl]phenyl 4-guanidinobenzoate.dihydrochloride White powder
IR (KBr): cm$^{-1}$ 3364, 1728, 1633, 1600, 1568, 1430, 1268, 1202.
$^1$H-NMR (DMSO-d6): δ

3.30–4.40(16H,m,—N N—,—N O—)

4.55(2H,s,CH$_2$CO)

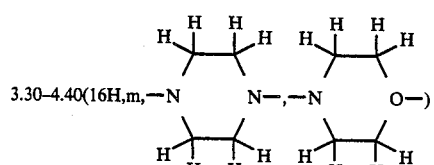

7.40–7.78(6H,m,N—COO—C)

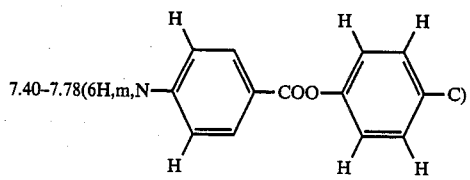

8.08(4H,br.s, C—NH)

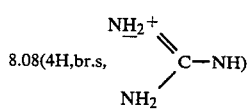

8.25(2H,d,N— )

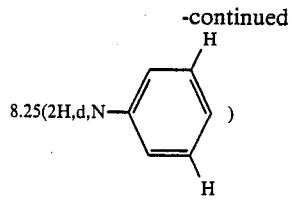

10.95(1H,s, C—NH—)

EXAMPLE 7

4-[4-(Pyrrolidinocarbonylmethyl)piperazino-carbonyl]-phenyl 4-guanidinobenzoate.dihydrochloride White powder
IR (KBr): cm$^{-1}$ 3350, 1729, 1631, 1601, 1565, 1260, 1200.
$^1$H-NMR (DMSO-d6): δ

1.70~2.14(4H,br.,—N )

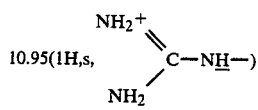

3.20~4.20(14H,br.N—CH$_2$×7)

7.38~7.80(6H,m,N— —COO— —C)

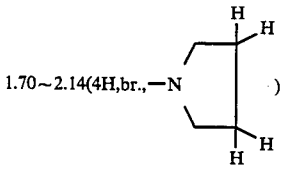

8.00~8.38(6H,m,N— , C—NH—)

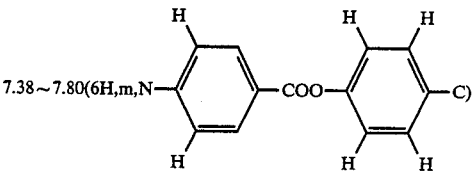

11.04(1H,s, C—NH—)

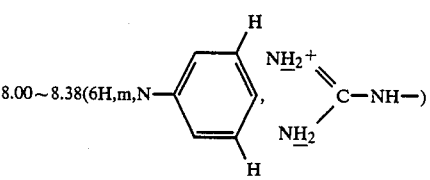

EXAMPLE 8

4-[2-(4-Isopropylpiperazinocarbonyl)ethenyl]-3-methoxyphenyl 4-guanidinobenzoate.dihydrochloride Melting Point: 224°–229° C. (decomposed)
IR (KBr): cm$^{-1}$ 3367, 1727, 1671, 1642, 1599, 1234.
$^1$H-NMR (DMSO-d6): δ

1.36(6H,d,CH(CH$_3$)(CH$_3$))

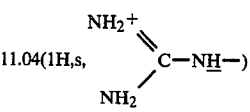

3.00~3.74(9H,br.N—CH$_2$×4,N—CH)

3.88(3H,s,OCH$_3$)

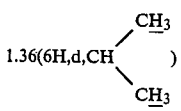

7.26~7.80 (7H, m, Ar-H of N⟨C₆H₃⟩-COO-⟨C₆H₃⟩-C,CH=CH-, with OH)

8.00 (4H, br.s, NH₂⁺-C(NH₂)-NH-)

7.22 (2H, d, Ar-H)

10.72 (1H, s, NH₂⁺-C(NH₂)-NH-)

EXAMPLE 9

4-[4-(Isopropylcarbamoylmethyl)piperazinocarbonyl]phenyl 4-guanidinobenzoate.dihydrochloride White powder
IR (KBr): cm⁻¹ 3321, 1726, 1664, 1618, 1562, 1260, 1200.

¹H-NMR (DMSO-d6): δ

1.10 (6H, d, CH(CH₃)₂)

3.20~4.18 (11H, br. N-CH₂×5, N-CH)

7.28~7.68 (6H, m, Ar-H of N-C₆H₄-COO-C₆H₄-C)

7.86~8.24 (6H, m, Ar-H, NH₂⁺-C(NH₂)-NH-)

8.64~8.80 (1H, br. -CONH-)

10.86 (1H, s, NH₂⁺-C(NH₂)-NH-)

EXAMPLE 10

4-[4-(Ethoxycarbonylmethyl)piperazinocarbonyl]phenyl 4-guanidinobenzoate.dihydrochloride White powder
IR (KBr): cm⁻¹ 3353, 1734, 1671, 1623, 1600, 1566, 1263, 1201.

¹H-NMR (DMSO-d6): δ

1.46 (3H, t, CH₂-CH₃)

3.30~4.10 (10H, m, N-CH₂×5)

4.24 (2H, q, -CH₂-CH₃)

7.34~7.66 (6H, m, Ar-H of N-C₆H₄-COO-C₆H₄-C)

7.90~8.26 (6H, m, Ar-H, NH₂⁺-C(NH₂)-NH-)

10.84 (1H, s, NH₂⁺-C(NH₂)-NH-)

EXAMPLE 11

4-(4-Isopropylpiperazinocarbonyl)-3,5-dimethoxyphenyl 4-gunanidinobenzoate.dihydrochloride Melting Point: 197°-199° C. (decomposed).
IR (KBr): cm⁻¹ 3362, 1723, 1625, 1598, 1125.

¹H-NMR (CD₃OD): δ

1.44 (6H, d, -CH(CH₃)₂)

3.12~3.80 (9H, m, N-CH₂×4, N-CH)

3.82 (6H, s, OCH₃×2)

6.88 (2H, s, COO-C₆H₂(OH)₂-C)

7.42 (2H, d, Ar-H)

8.18 (2H, d, N-Ar-H)

EXAMPLE 12

4-[4-(Piperidinocarbonylmethyl)piperazinocarbonyl]phenyl 4-guanidinobenzoate.dihydrochloride White powder
IR (KBr): cm$^{-1}$ 3365, 1729, 1633, 1586, 1259, 1202.
$^1$H-NMR (DMSO-d6): δ

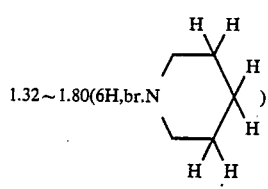
1.32~1.80(6H,br.N )

3.20~4.14(14H,br.N—CH$_2$×7)

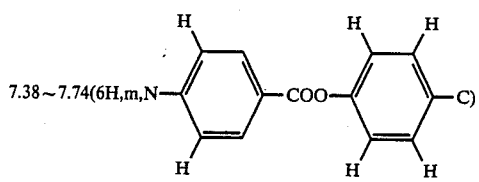
7.38~7.74(6H,m,N —COO— C)

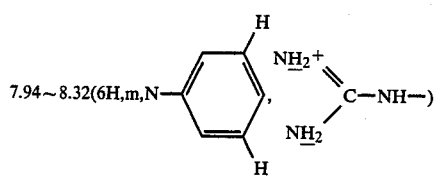
7.94~8.32(6H,m,N— , C—NH—)

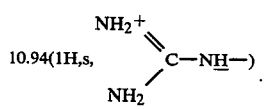
10.94(1H,s, C—NH—)

EXAMPLE 13

4-(4-Isopropylpiperazinocarbonyl)phenyl 4-guanidinobenzoate.dihydrochloride

Melting Point: 223°–225° C.
IR (KBr): cm$^{-1}$ 3500–2900, 1725, 1600, 1260.
$^1$H-NMR (DMSO-d6): δ

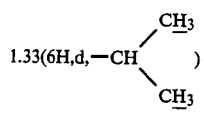
1.33(6H,d,—CH )

3.04~3.80(9H,br.N—CH$_2$×4,N—CH)

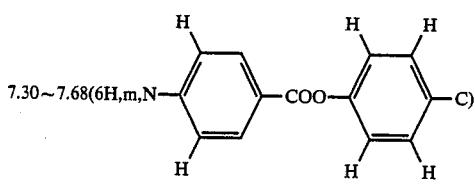
7.30~7.68(6H,m,N— —COO— C)

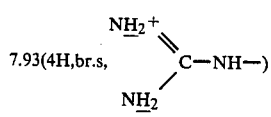
7.93(4H,br.s, C—NH—)

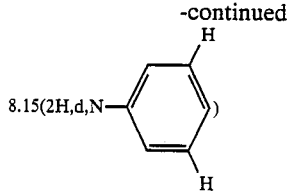
8.15(2H,d,N )

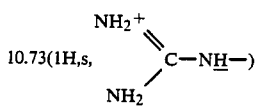
10.73(1H,s, C—NH—)

EXAMPLE 14

4-(4-Isopropylpiperazinocarbonyl)-3-methoxylphenyl 4-guanidinobenzoate.dihydrochloride White powder
IR (KBr): cm$^{-1}$ 3500–2800, 1727, 1670, 1595, 1254.
$^1$H-NMR (DMSO-d6): δ

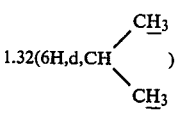
1.32(6H,d,CH )

3.00~3.88(12H,m,N—CH$_2$×4,N—CH,OCH$_3$)

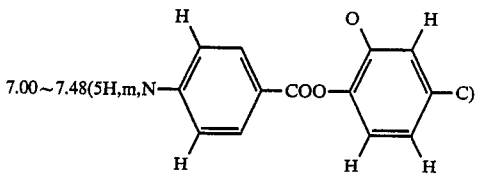
7.00~7.48(5H,m,N— —COO— C)

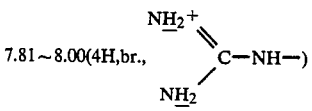
7.81~8.00(4H,br., C—NH—)

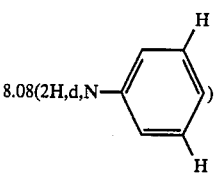
8.08(2H,d,N )

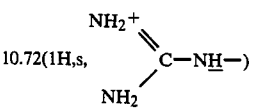
10.72(1H,s, C—NH—)

EXAMPLE 15

4-[4-(2-Isopropylaminocarbonylethyl)piperazinocarbonyl]phenyl 4-guanidinobenzoate.dihydrochloride Melting Point: 155°–158° C. (decomposed).
IR (KBr): cm$^{-1}$ 3305, 1731, 1640, 1599, 1508, 1454, 1428, 1257, 1199.
$^1$H-NMR (DMSO-d6): δ

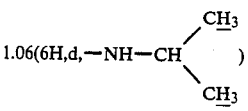
1.06(6H,d,—NH—CH )

-continued 2.60-2.70(2H,m,—CH₂—CO)

3.0-3.60(10H,m, 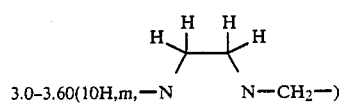 )

3.74-3.84(1H,m,—CH—)

7.40(2H,d,O 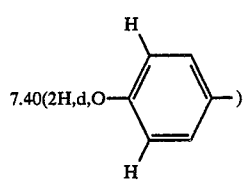 )

7.45(2H,d,N 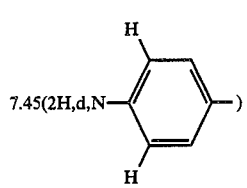 )

7.60(2H,d,O 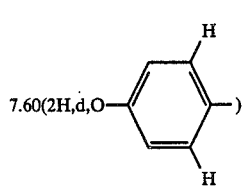 )

7.84(4H,br.s, 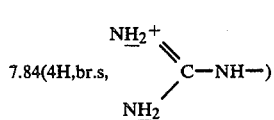 )

8.04-8.12(1H,m,—CO—NH—)

8.17(2H,d,N 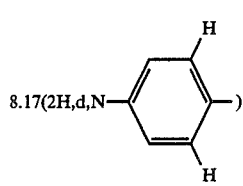 )

10.40(1H,s, 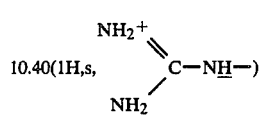 )

EXAMPLE 16

4-[4-(2-Oxopyrrolidinocarbonylmethyl)piperazinocarbonyl]phenyl 4-guanidinobenzoate.dihydrochloride Melting Point: 196°-198° C. (decomposed).

IR (KBr): cm⁻¹ 3351, 1729, 1673, 1600, 1565, 1529, 1199.

¹H-NMR (DMSO-d6): δ

1.90-2.24(2H,m,—N 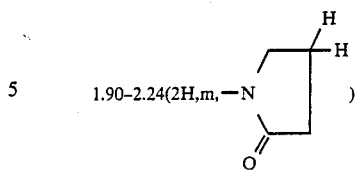 )

2.50-2.76(2H,t,—N 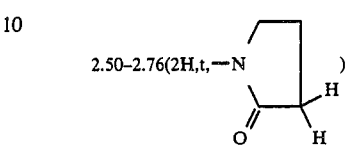 )

3.30-4.10(10H,m,—N 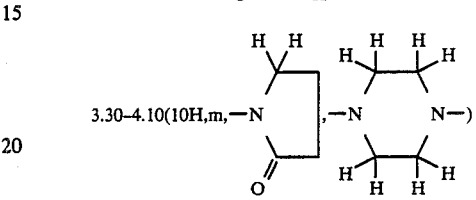 )

4.62(2H,s,—CH₂CO—)

7.36-7.76(6H,m,N 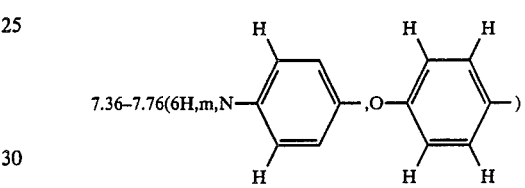 )

8.08(4H,br.s, 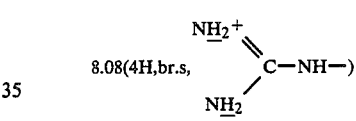 )

8.24(2H,d,N 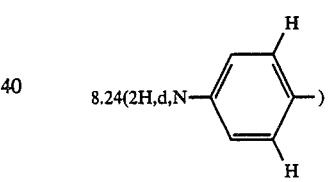 )

11.18(1H,s, 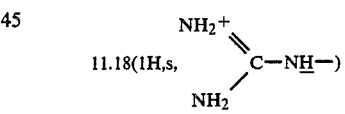 )

EXAMPLE 17

4-[4-(2-Methoxycarbonylpyrrolidinocarbonylmethyl)-piperazinocarbonyl]phenyl 4-guanidinobenzoate.dihydrochloride Melting Point: 193°-195° C. (decomposed).

IR (KBr): cm⁻¹ 3320, 1728, 1618, 1600, 1564, 1431, 1256, 1196, 1161.

¹H-NMR (DMSO-d6): δ

1.70-2.30(4H,m,—N 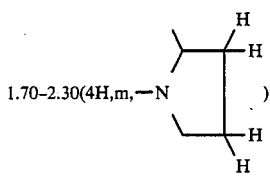 )

2.95(2H,br.s,—N⟨ ⟩)

3.26–3.90(13H,m,N—CH₂×5,CH₃)

4.68–4.88(1H,m,CH)

7.35–7.72(6H,m,N—⟨C₆H₄⟩—O—⟨C₆H₄⟩—CO—)

8.02(4H,br.s, NH₂⁺—C(NH₂)—NH—)

8.24(2H,d,N—⟨C₆H₄⟩—)

10.88(1H,s, NH₂⁺—C(NH₂)—NH—)

EXAMPLE 18

4-[4-(4-Methylpiperidinocarbonylmethyl)-piperazinocarbonyl]phenyl 4-guanidinobenzoate.dihydrochloride Light yellow powder
IR (KBr): cm⁻¹ 3353, 1732, 1634, 1600, 1566, 1259, 1200.
¹H-NMR (DMSO-d6): δ

0.91 (3H, d, CH—CH₃)

1.09 (2H, m, —CH₂—)

1.66 (3H, m, —CH₂—, —N⟨CH₃, H⟩)

2.63 (1H, t, —N⟨ ⟩)

3.03 (1H, t, —N⟨ ⟩)

3.37 (6H, br. s, —CH₂CO, —CO—N⟨ ⟩N)

3.66 (3H, m, —CO—N⟨ ⟩N, —N⟨ ⟩)

4.31 (3H, m, N⟨ ⟩N, —N⟨ ⟩)

7.31–7.60 (6H, m, N—⟨C₆H₄⟩—O—⟨C₆H₄⟩—)

7.97 (4H, br. s, NH₂⁺—C(NH₂)—NH—)

8.17 (2H, d, N—⟨C₆H₄⟩—)

10.77 (1H, s, NH₂⁺—C(NH₂)—NH—)

EXAMPLE 19

4-[4-(Ethoxycarbonylmethylcarbamoylmethyl)-piperazinocarbonyl]phenyl 4-guanidinobenzoate.dihydrochloride Light yellow powder
IR (KBr): cm⁻¹ 3326, 1731, 1672, 1621, 1598, 1557, 1258, 1199.
¹H-NMR (DMSO-d6): δ

1.49 (3H, t, CH₂—CH₃)

3.40 (10H, m, −N(CH₂CH₂)₂N−CH₂CO) 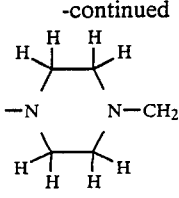

3.97 (2H, d, −NHCH₂−)
4.14 (2H, q, −CH₂−CH₃)

7.31–7.66 (6H, m, N-C₆H₄-O-C₆H₅) 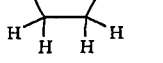

8.20 (2H, d, N-C₆H₄-) 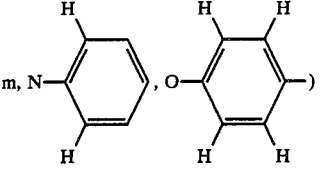

7.94 (4H, br. s, H₂N⁺=C(NH₂)−NH−) 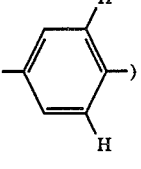

9.17 (1H, br. s, −CONHCH₂−)

10.69 (1H, s, H₂N⁺=C(NH₂)−NH−) 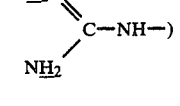

EXAMPLE 20

4-[4-Phenylcarbamoylmethylpiperazinocarbonyl]phenyl 4-guanidinobenzoate·dihydrochloride Colorless powder
IR (KBr): cm⁻¹ 3303, 3171, 1725, 1669, 1596, 1433, 1255, 1198.
¹H-NMR (DMSO-D6): δ

3.30–3.60 (4H, m, CO−N(CH₂CH₂)N) 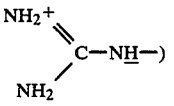

3.66–4.06 (4H, m, CO−N(CH₂CH₂)N) 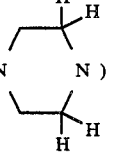

4.28 (2H, br. s, −CH₂CO−)

7.14–7.80 (6H, m, N-C₆H₄-O-C₆H₅) 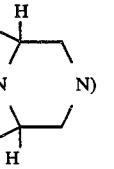

8.08 (4H, br. s, H₂N⁺=C(NH₂)−NH−) 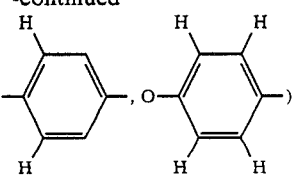

8.26 (2H, d, N-C₆H₄-) 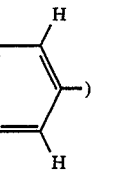

10.90 (1H, s, H₂N⁺=C(NH₂)−NH−) 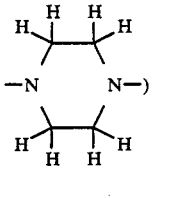

11.12 (1H, br. s, −CONH−)

EXAMPLE 21

4-[4-(1-Carbamoylethyl)piperazinocarbonyl]phenyl 4-guanidinobenzoate·dihydrochloride White powder
IR (KBr) cm⁻¹ 3375, 3178, 1728, 1675, 1622, 1602, 1567, 1462, 1436, 1251, 1201.
¹H-NMR (DMSO-d6): δ

1.47–1.50 (3H, d, −CH₃)

3.10–3.80 (8H, m, −N(CH₂CH₂)₂N−) 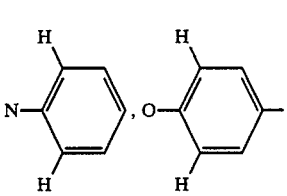

3.96 (1H, m, −CH−CH₃)

7.37–7.48 (4H, m, N-C₆H₄-O-C₆H₄-) 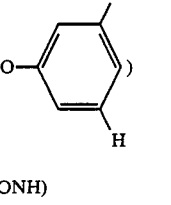

7.58–7.63 (2H, d, O-C₆H₄-)

7.80 (1H, br. s, CONH)

7.96 (4H, br. s, 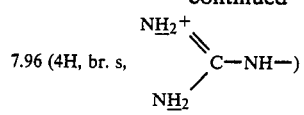)

8.15–8.19 (2H, d, 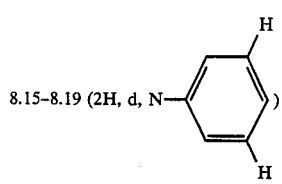)

8.26 (1H, br. s, CONH)

10.75 (1H, s, 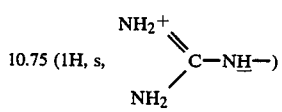)

EXAMPLE 22

4-[4-[1-(2-Dimethylaminoethylcarbamoyl)ethyl]-piperazinocarbonyl]phenyl 4-guanidinobenzoate.trihydrochloride Powder
IR (KBr): cm$^{-1}$ 3367, 1726, 1667, 1600, 1565, 1461, 1261, 1200.
$^1$H-NMR (DMSO-d6): δ

1.20–1.50 (3H, m, —CH—CH$_3$)
2.80 (6H, s, N—CH$_3$ × 2)
3.08–4.10 (12H, m, N—CH$_2$ × 6)

7.32–7.70 (6H, m, 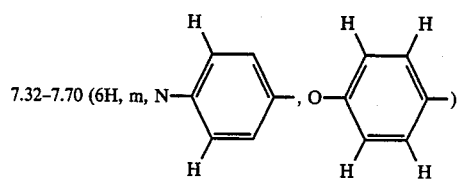)

8.02 (4H, br. s, 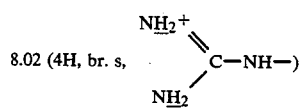)

8.22 (2H, d, 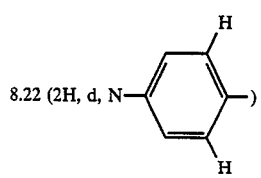)

8.80–9.20 (1H, m, —CONH—)

10.82 (1H, br. s, 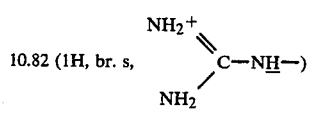)

EXAMPLE 23

4-[4-(2-Aminoethyl)piperazinocarbonyl]phenyl 4-guanidinobenzoate.trihydrochoride Light brown powder
IR (KBr) cm$^{-1}$ 3387, 1726, 1669, 1600, 1568, 1458, 1262, 1201.

$^1$H-NMR (DMSO-d6): δ

2.60–3.20 (7H, m, CH$_2$CH$_2$NH$_3$$^+$)

3.44–3.80 (8H, m, )

7.30–7.68 (6H, m, 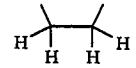)

8.00 (4H, br. s, 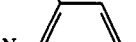)

8.22 (2H, d, 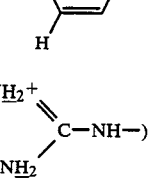)

10.10–10.90 (1H, m, 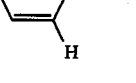)

EXAMPLE 24

4-[4-(2-Acetylaminoethyl)piperazinocarbonyl]phenyl 4-guanidinobenzoate.dihydrochloride Powder
IR (KBr): cm$^{-1}$ 3360, 1729, 1622, 1600, 1565, 1429, 1263, 1201.
$^1$N-NMR (DMSO-d6): δ

1.92 (3H, s, —CH$_3$)
2.90–3.80 (12H, m, —N—CH$_2$—CH$_2$—N— × 3)

7.28–7.64 (6H, m, 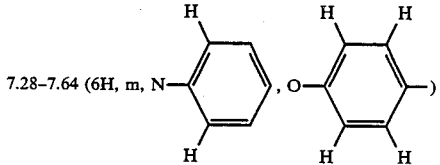)

7.98 (4H, br. s, 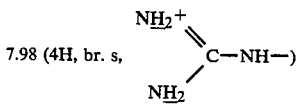)

8.10 (2H, d, 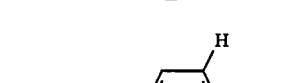)

8.14 (1H, br. s, —NHCO)

10.66 (1H, s, 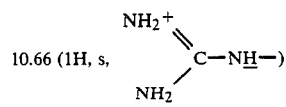)

EXAMPLE 25

4-[4-(2-Benzyloxycarbonylaminoethyl)piperazinocarbonyl]phenyl 4-guanidinobenzoate.dihydrochloride Melting Point: 183°–185° C. (decomposed).
IR (KBr): cm$^{-1}$ 3307, 1726, 1670, 1630, 1600, 1568, 1262, 1202.
$^1$H-NMR (DMSO-d6): δ

3.00–3.23 (4H, m, —N—CH$_2$—CH$_2$—NH—)

3.24–3.70 (8H, m, 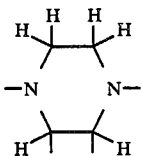)

5.04 (2H, s, —COOCH$_2$—)

7.24–7.64 (6H, m, 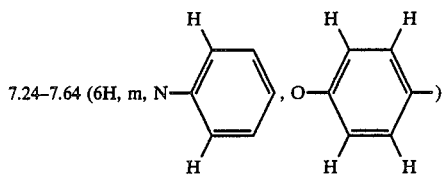)

7.98 (4H, br. s, 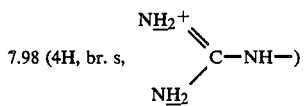)

8.10 (2H, d, 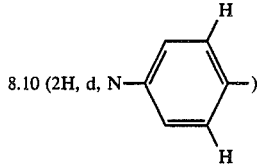)

10.66 (1H, s, 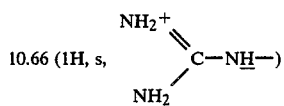)

11.42 (1H, br. s, NHCO)

EXAMPLE 26

4-[4-(2-Dimethylaminoethyl)piperazinocarbonyl]phenyl 4-guanidinobenzoate.trihydrochloride Melting Point: 202°–204° C.
IR (KBr): cm$^{-1}$ 3395, 1719, 1677, 1622, 1598, 1565, 1267, 1200.
$^1$H-NMR (DMSO-d6): δ

2.70 (2H, m, 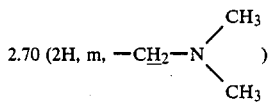)

2.78 (6H, s, 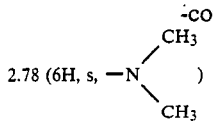)

3.20 (2H, m, 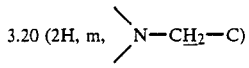)

3.30–3.80 (8H, m, 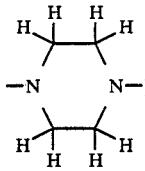)

7.35–7.55 (6H, m, 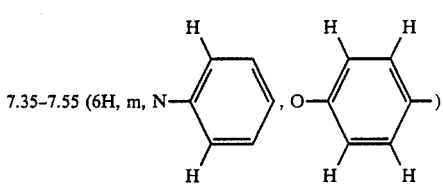)

7.95 (4H, br. s, 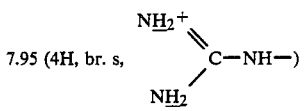)

8.19 (2H, d, 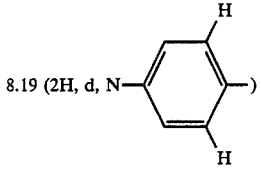)

10.72 (1H, br. s, 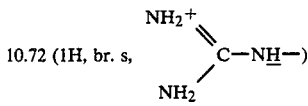)

EXAMPLE 27

4-[4-(Guanidinobenzoyloxy)benzoyl]piperazino-acetic acid:dihydrochloride

Colorless powder
IR (KBr) cm$^{-1}$ 3373, 1728, 1672, 1620, 1600, 1566, 1431, 1261, 1200.
$^1$H-NMR (DMSO-d6): δ

3.28–3.60 (4H, m, )

3.72–4.02 (4H, m, 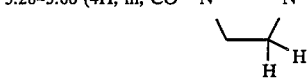)

4.20 (2H, br. s, —CH$_2$COOH)

7.36-7.78 (6H, m, 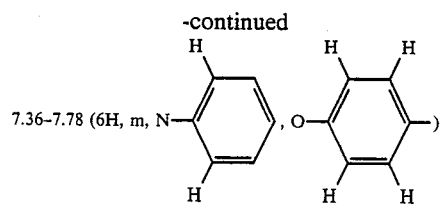)
8.04 (4H, br. s, 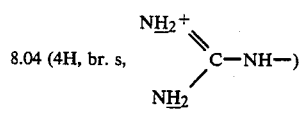)
8.24 (2H, d, 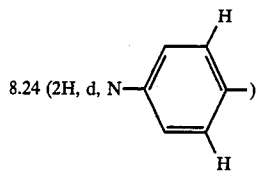)
10.86 (1H, s, 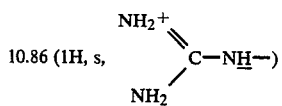)
EXAMPLE 28
4-(4-Benzyloxycarbonylmethylpiperazinocarbonyl)-phenyl 4-guanidinobenzoate.dihydrochloride
Light brown powder
IR (KBr): cm$^{-1}$ 3381, 1735, 1671, 1626, 1600, 1264, 1201.
$^1$H-NMR (DMSO-d6): δ
3.20-3.52 (4H, m, 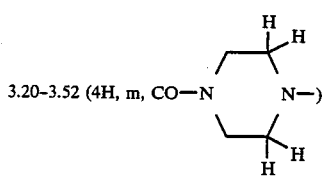)
3.64-4.04 (4H, m, 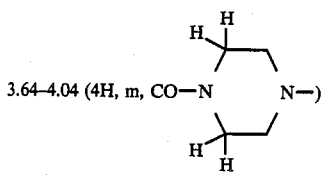)
4.28 (2H, s, CH$_2$CO), 5.30 (2H, s, OCH$_2$)
7.36-7.74 (11H, m, 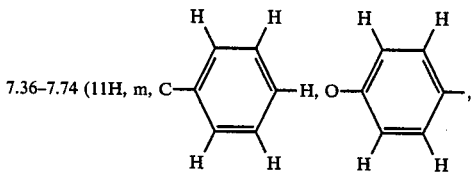, )
8.02 (4H, br. s, 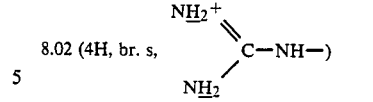)
8.24 (2H, d, 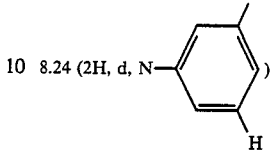)
10.82 (1H, s, 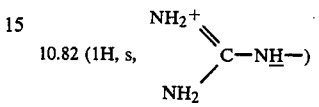)
EXAMPLE 29
4-Piperazinocarbonylphenyl 4-guanidinobenzoate.dihydrochloride
Melting Point: 200°-226° C. (decomposed).
IR (KBr): cm$^{-1}$ 3364, 1728, 1672, 1617, 1600, 1565, 1434, 1264, 1201.
$^1$H-NMR (DMSO-d6): δ
3.04-3.50 (5H, m, 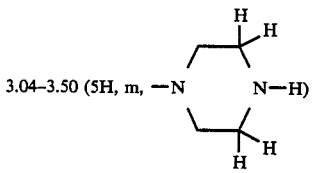)
3.64-3.90 (4H, m, 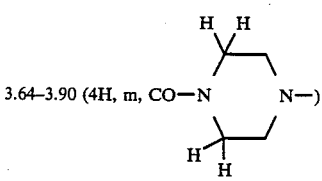)
7.36-7.72 (6H, m, 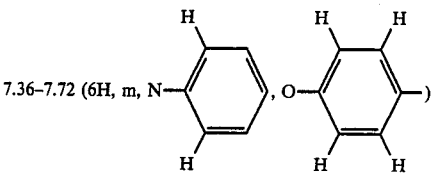)
7.96 (4H, br. s, 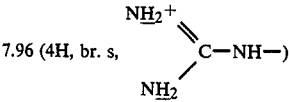)
8.22 (2H, d, 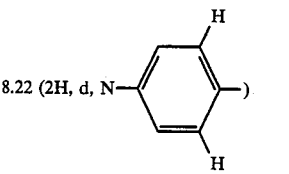)
10.00 (1H, br. s, 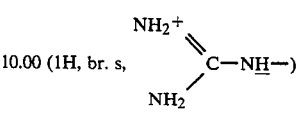)

EXAMPLE 30

4-(4-Methylpiperazinocarbonyl)phenyl 4-guanidinobenzoate.dihydrochloride

Melting Point: 197°–199° C. (decomposed).
IR (KBr): cm$^{-1}$ 3348, 1738, 1673, 1662, 1599, 1505, 1261, 1200, 1175.
$^1$H-NMR (DMSO-d6): δ

2.76 (3H, s, —CH$_3$)

3.12–3.40 (4H, m, 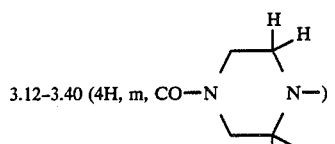)

3.60–4.08 (4H, m, 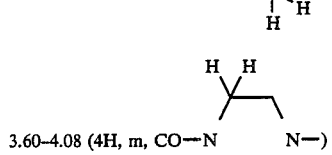)

7.38–7.72 (6H, m, 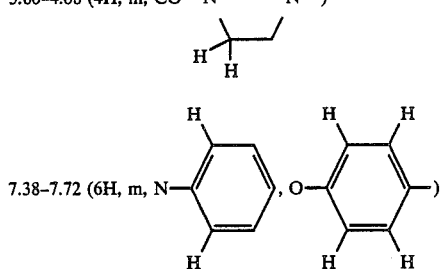)

8.02 (4H, br. s, 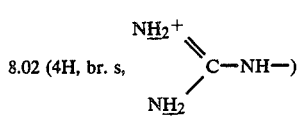)

8.24 (2H, d, 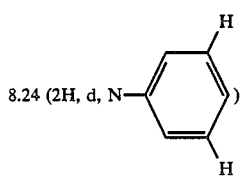)

10.84 (1H, br. s, 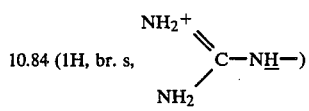)

EXAMPLE 31

4-[4-(Cyclohexylmethyl)piperazinocarbonyl]phenyl 4-guanidinobenzoate.carbonate

Colorless powder
IR (KBr): cm$^{-1}$ 3326, 2909, 1726, 1691, 1624, 1604, 1566, 1259, 1199.
$^1$H-NMR (DMSO-d6): δ

0.60–1.84 (11H, m, 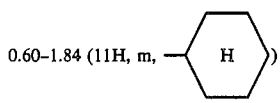)

2.14 (2H, d, 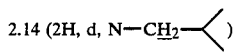)

2.26–2.48 (4H, m, 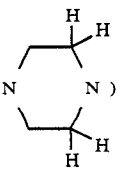)

3.40–3.70 (4H, m, 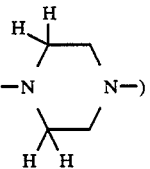)

5.60 (4H, br. s, 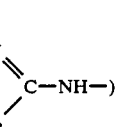)

6.96 (2H, d, 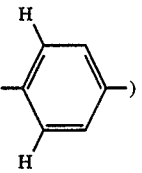)

7.42 (4H, q, 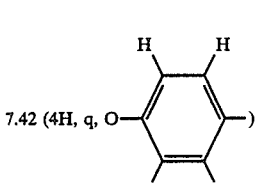)

7.98 (2H, d, 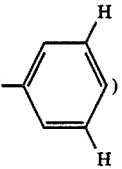)

EXAMPLE 32

4-(4-Benzylpiperazinocarbonyl)phenyl 4-guanidinobenzoate.dihydrochloride

Melting Point: 202°–210° C. (decomposed).
IR (KBr): cm$^{-1}$ 3377, 1731, 1673, 1622, 1601, 1508, 1454, 1261, 1201.
$^1$H-NMR (DMSO-d6): δ

3.00–3.70 (8H, m, 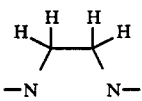)

4.35 (2H, br. s, 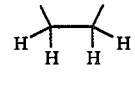)

7.36–7.80 (11H, m, —CH₂—C₆H₅ and aromatic H)

8.00 (4H, br. s, guanidino NH₂⁺/NH₂/NH)

8.24 (2H, d, aromatic H ortho to N)

10.80 (1H, s, guanidino NH)

EXAMPLE 33

4-(4-Carbamoylmethylhomopiperazinocarbonyl)phenyl 4-guanidinobenzoate.dihydrochloride

Melting Point: 217°–220° C. (decomposed).
IR (KBr): cm⁻¹ 3315, 1722, 1679, 1623, 1599, 1275, 1195.
¹H-NMR (DMSO-d6): δ

1.30–1.90 (2H, m, —N—CH₂—CH₂—CH₂—N—)

3.20–3.80 (8H, m, —N(CH₂)₂N(CH₂)₂—)

4.00 (2H, m, N—CH₂—CO)

7.39 (2H, d, aromatic H ortho to O)

7.45 (2H, d, aromatic H ortho to N)

7.58 (2H, d, aromatic H ortho to O)

7.71 (1H, s, —CONH)

7.94 (4H, br. s, guanidino NH₂⁺/NH₂/NH)

8.11 (1H, s, —CONH)

8.17 (2H, d, aromatic H ortho to N)

10.70 (1H, s, guanidino NH)

EXAMPLE 34

4-(N,N-Dimethylethylenediaminocarbonyl)phenyl 4-guanidinobenzoate.dihydrochloride

Melting Point: 217°–222° C. (decomposed).
IR (KBr): cm⁻¹
3256, 2974, 1725, 1680, 1627, 1601, 1559, 1256, 1209.
¹H-NMR (DMSO-d6): δ

2.83 (6H, s, —N(CH₃)₂)

3.20–3.35 (2H, m, —CH₂—N(CH₃)₂)

3.60–3.75 (2H, m, NH—CH₂—CH₂)

7.41 (2H, d, aromatic H ortho to O)

-continued 7.45 (2H, d, 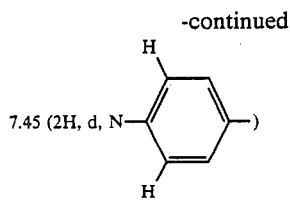)

7.94 (4H, s, 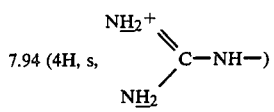)

8.07 (2H, d, 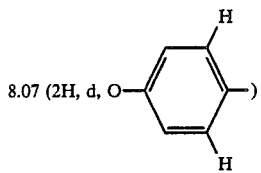)

8.17 (2H, d, 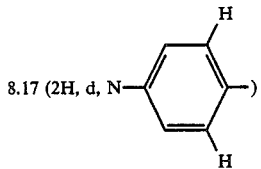)

9.03 (1H, m, —CONH)

10.67 (1H, s, 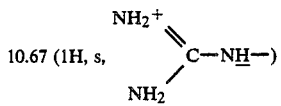)

EXAMPLE 35

4-(2-Piperizinoethylcarbamoyl)phenyl 4-guanidinobenzoate.dihydrochloride

Melting Point: 207°–209° C.
IR (KBr): cm$^{-1}$ 3260, 1728, 1652, 1576, 1500, 1266.
$^1$H-NMR (DMSO-d6): δ

1.30–2.00 (6H, m, 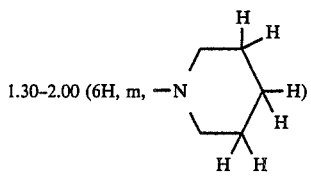)

2.72–3.86 (8H, m, —CH$_2$CH$_2$—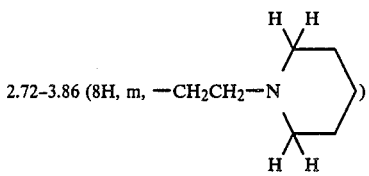)

7.38–7.60 (4H, m, 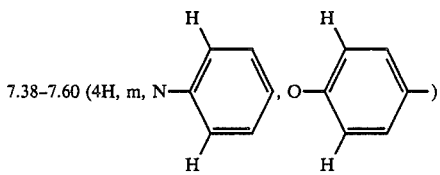)

-continued 7.98 (4H, br. s, 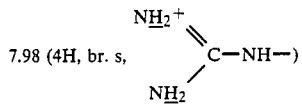)

8.08–8.32 (4H, m, 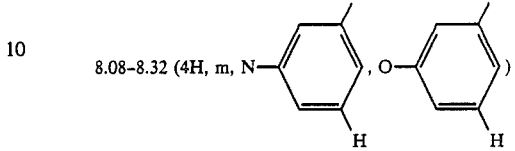)

9.06–9.24 (1H, m, CONH)

10.72 (1H, m, 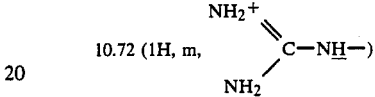)

EXAMPLE 36

4-(2-Morpholinoethylcarbamoyl)phenyl 4-guanidinobenzoate.dihydrochloride

Melting Point: 240°–243° C.
IR (KBr): cm$^{-1}$ 3374, 1730, 1652, 1630, 1575, 1268, 1167
$^1$H-NMR (DMSO-d6): δ

3.00–4.12 (12H, m, —CH$_2$CH$_2$—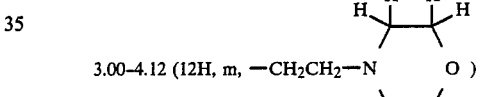)

7.40–7.60 (4H, q, 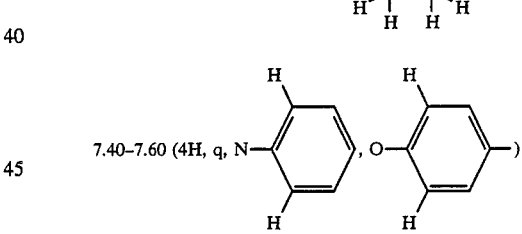)

8.04 (4H, br. s, 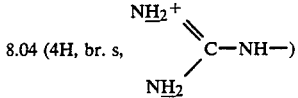)

8.14–8.36 (4H, q, 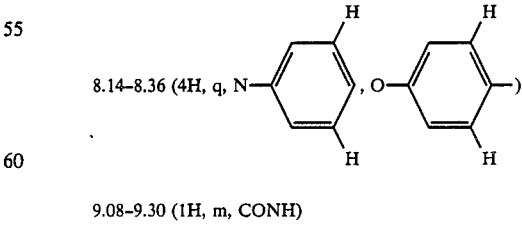)

9.08–9.30 (1H, m, CONH)

10.84 (1H, s, 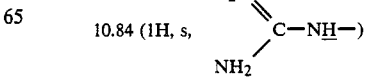)

EXAMPLE 37

4-(N,N,N'-Trimethylethylenediaminocarbonyl)phenyl 4-guanidinobenzoate.dihydrochloride Melting Point: 229°–231° C.
IR (KBr): cm$^{-1}$ 3430, 3340, 1721, 1686, 1616, 1600, 1533, 1260, 1206. $^1$H-NMR (DMSO-d6): δ

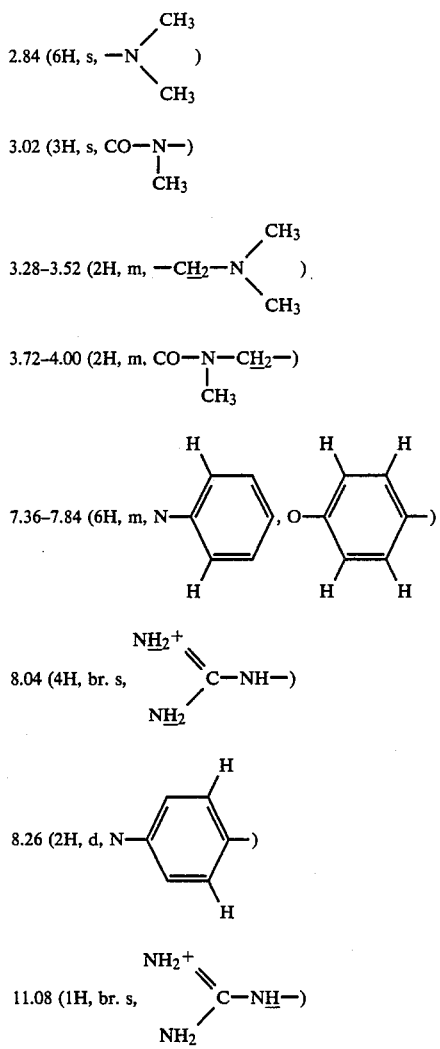

EXAMPLE 38

4-[(N-Carbamoylmethyl-N,N'-dimethylethylenediamino)carbonyl]phenyl 4-guanidinobenzoate.dihydrochloride Melting Point: 245°–249.5° C. (decomposed).
IR (KBr): cm$^{-1}$ 3142, 1724, 1685, 1615, 1564, 1258, 1207.
$^1$H-NMR [D$_2$O-CD$_3$OH (1:3)]: δ

3.14 (6H, s, CH$_3$ × 2)

3.58 (2H, br. s, CO—N—CH$_2$—CH$_2$—N—)
           |                |
          CH$_3$           CH$_3$ 4.00 (2H, br. s, CO—N—CH$_2$—CH$_2$—N—)
           |                |
          CH$_3$           CH$_3$ 4.16 (2H, s, —CH$_2$CONH$_2$)

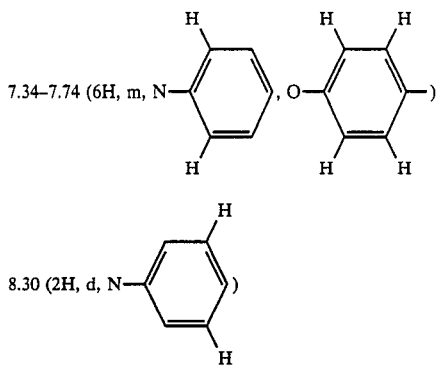

What is claimed is:
1. A benzoyl ester of the following formula (I), and acid addition salts thereof,

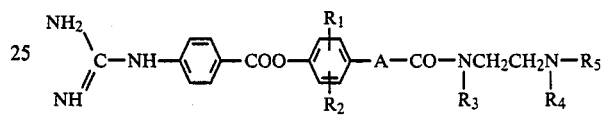

in which R$_1$ and R$_2$ are the same or different and represent a hydrogen atom or a lower alkoxy group having from 1 to 6 carbon atoms; A represents a single bond, or a linear or branched lower alkylene group or a lower alkenylene group having 1 to 6 carbon atoms; R$_3$ and R$_4$ are the same or different and represent a hydrogen atom or a lower alkyl group, or R$_3$ and R$_4$ join together to form a lower alkylene group having from 2 to 6 carbon atoms; R$_5$ represents a group of the formula, —X—(CO)$_n$—Y in which X represents a single bond, or a linear or branched lower alkylene group or alkenylene group having from 1 to 6 carbon atoms; n is 0 or 1; Y represents a hydrogen atom, a cycloalkyl group having from 3 to 8 carbon atoms, a phenyl group, a naphthyl group, a hydroxyl group, a lower alkoxy group having from 1 to 6 carbon atoms, a benzyloxy group or a group of the formula,

in which R$_6$ and R$_7$ are the same or different and represent a hydrogen atom, a linear or branched lower alkyl group having from 1 to 6 carbon atoms, a phenyl group, a naphthyl group, a lower alkylcarbonyl group having from 2 to 7 carbon atoms, a lower alkoxycarbonyl group having from 2 to 7 carbon atoms, a benzyloxycarbonyl group, an alkoxycarbonylalkyl group in which each alkyl group has from 1 to 6 carbon atoms, an aminoalkyl group having from 1 to 6 carbon atoms, a monoalkylaminoalkyl group in which each alkyl group has from 1 to 6 carbon atoms, or join together to form a heterocyclic ring selected from the group consisting of pyrrolidine, piperidine, morpholine, piperazine, and homopiperazine, and the ring may be substituted by a lower alkyl group having from 1 to 6 carbon atoms, a hydroxyl group, a lower alkoxy group having 1 to 6 carbon atoms, a lower alkoxycarbonyl group having from 1 to 6 carbon atoms or an oxo group, or R$_4$ and R$_5$ join together to form a heterocyclic ring selected from the group consisting of piperidine and morpholine.

2. A compound according to claim 1, wherein $R_1=R_2=H$.

3. A compound according to claim 1, wherein $R_3$ and $R_4$ are —$CH_2CH_2$—.

4. A compound according to claim 1, which is 4-[4-(carbamoylmethyl)piperazinocarbonylmethyl]phenyl 4-guanidinobenzoate.

5. A compound according to claim 1, which is 4-[4-(carbamoylmethyl)piperazinocarbonyl]-phenyl 4-gunidinobenzoate.

6. A compound according to claim 1, which is 4-[2-(4-(carbamoylmethyl)piperazinocarbonyl)ethenyl]phenyl 4-guanidinobenzoate.

7. A compound according to claim 1, which is 4-[4-(dimethylcarbamoylmethyl)piperazinocarbonyl]-phenyl 4-guanidinobenzoate.

8. A compound according to claim 1, which is 4-[2-(4-(carbamoylmethyl)piperazinocarbonyl)ethyl]-phenyl 4-guanidinobenzoate.

9. A compound according to claim 1, which is 4-[4-(morpholinocarbonylmethyl)piperazinocarbonyl]-phenyl 4-guanidinobenzoate.

10. A compound according to claim 1, which is 4-[4-(pyrrolidinocarbonylmethyl)piperazinocarbonyl]phenyl 4-guanidinobenzoate.

11. A compound according to claim 1, which is 4-[4-(isopropylcarbamoylmethyl)piperazinocarbonylmethyl]-phenyl 4-guanidinobenzoate.

12. A compound according to claim 1, which is 4-[4-(ethoxycarbonylmethyl)piperazinocarbonyl]-phenyl 4-guanidinobenzoate.

13. A compound according to claim 1, which is 4-[4-(piperidinocarbonylmethyl)piperazinocarbonyl]-phenyl 4-guanidinobenzoate.

14. A compound according to claim 1, which is 4-[4-(isopropylpiperazinocarbonyl)phenyl 4-guanidinobenzoate.

15. A compound according to claim 1, which is 4-[4-(2-isopropylcarbamoylethyl)piperazinocarbonyl]-phenyl 4-guanidinobenzoate.

16. A compound according to claim 1, which is 4-[4-(2-oxopyrrolidinocarbonylmethyl)piperazinocarbonyl]-phenyl 4-guanidinobenzoate.

17. A compound according to claim 1, which is 4-[4-(2-methoxycarbonylpyrrolidinocarbonylmethyl)-piperazinocarbonyl]-phenyl 4-guanidinobenzoate.

18. A compound according to claim 1, which is 4-[4-(4-methylpiperidinocarbonylmethyl)-piperazinocarbonyl]-phenyl 4-guanidinobenzoate.

19. A compound according to claim 1, which is 4-[4-ethoxycarbonylmethylcarbamoylmethyl)-piperazinocarbonylmethyl]-phenyl 4-guanidinobenzoate.

20. A compound according to claim 1, which is 4-[4-phenylcarbonylmethylpiperazinocarbonyl]-phenyl 4-guanidinobenzoate.

21. A compound according to claim 1, which is 4-[4-(1-carbamoylethyl)piperazinocarbonyl]-phenyl 4-guanidinobenzoate.

22. A compound according to claim 1, which is 4-[4-[1-(2-dimethylaminoethylcarbamoyl)ethyl]-piperazinocarbonyl]-phenyl 4-guanidinobenzoate.

23. A compound according to claim 1, which is 4-(4-methylpiperazinocarbonyl]-phenyl 4-guanidinobenzoate.

24. A compound according to claim 1, which is 4-(4-carbamoylmethylhomopiperazinocarbonyl]-phenyl 4-guanidinobenzoate.

25. A compound according to claim 1, which is 4-(N,N-dimethylethylenediaminocarbonyl)-phenyl 4-guanidinobenzoate.

26. A compound according to claim 1, which is 4-(2-piperazinoethylcarbamoyl)-phenyl 4-guanidinobenzoate.

27. A compound according to claim 1, which is 4-(2-morpholinoethylcarbamoyl)-phenyl 4-guanidinobenzoate.

28. A compound according to claim 1, which is 4-(N,N,N'-trimethylethylenediaminocarbonyl)-phenyl 4-guanidinobenzoate.

29. A compound according to claim 1, which is 4-[(N-carbamoylmethyl-N,N'-dimethylethylenediamino)carbonyl]-phenyl 4-guanidinobenzoate.

* * * * *